United States Patent [19]

Katakura et al.

[11] Patent Number: 5,271,276
[45] Date of Patent: Dec. 21, 1993

[54] PHASE REGULATING APPARATUS OF ULTRASONIC MEASURING DEVICES

[75] Inventors: Kageyoshi Katakura, Tokyo; Toshio Ogawa, Chiba; Shin-ichi Kondo, Kodaira, all of Japan

[73] Assignees: Hitachi, Ltd.; Hitachi Medical Corporation, both of Tokyo, Japan

[21] Appl. No.: 797,025

[22] Filed: Nov. 25, 1991

[30] Foreign Application Priority Data

Nov. 28, 1990 [JP] Japan .................. 2-323164
Nov. 28, 1990 [JP] Japan .................. 2-323165
Nov. 28, 1990 [JP] Japan .................. 2-323166

[51] Int. Cl.⁵ ............................. G01N 29/04
[52] U.S. Cl. ............................. 73/626; 73/625; 128/661.01
[58] Field of Search .................. 73/626, 625; 128/661.01

[56] References Cited

U.S. PATENT DOCUMENTS

| | | | |
|---|---|---|---|
| 4,140,022 | 2/1979 | Masalak | 73/626 |
| 4,387,597 | 6/1983 | Brandestini | 73/626 |
| 4,550,607 | 11/1985 | Masalak et al. | 73/626 |
| 4,633,308 | 12/1986 | Dukes et al. | 128/661.01 |
| 4,662,223 | 5/1987 | Riley et al. | 73/625 |
| 4,700,573 | 10/1987 | Savord | 73/625 |
| 4,779,242 | 10/1988 | Lannuzel | 73/626 |

FOREIGN PATENT DOCUMENTS 20857 2/1977 Japan .

Primary Examiner—Hezron E. Williams
Assistant Examiner—Nashmiya Ashraf
Attorney, Agent, or Firm—Antonelli, Terry, Stout & Kraus

[57] ABSTRACT

A frequency transfer type phase adjustment apparatus for frequency-transferring a plurality of reception signals derived from arrayed ultrasonic transducer elements into low frequency components by mixing these reception signals with a reference signal, and for applying delays to these low frequency components so as to be summed with each other, comprises small delay circuits for applying very short delays to the respective reception signals before being frequency-transferred; and a quantizing delay circuit for applying delays obtained by multiplying a delay time unit by an integer, to the respective reception signals after being frequency-transferred. A ratio of the delay time unit to one-cycle period of the reference signal is equal to an integer ratio. Phase shifters are inserted into either the output sides or the input sides of the mixers for the respective signal channels used for the frequency transfer operation. These phase shifters are capable of selectable phase shift amounts from a finite number of phase shift amounts which have been prepared for compensating phase differences in the delayed reception signals.

14 Claims, 6 Drawing Sheets

PHASE REGULATING APPARATUS OF ULTRASONIC MEASURING DEVICES

BACKGROUND OF THE INVENTION

The present invention relates to an apparatus for performing either a detection or an examination of an object by way of ultrasonic waves, and more particularly to a phase adjustment apparatus for phasing signals received from a plurality of ultrasonic transducer elements.

Ultrasonic apparatuses in which delays are applied to reception signals of ultrasonic waves detected by a plurality of arrayed transducer elements, wave fronts of the ultrasonic waves derived from a desirable azimuth, or a desirable distance are set to be the same phases, and these ultrasonic waves signals are summed with each other to obtain improved azimuth resolution, have been widely utilized in various technical fields such as a flaw examination for an object, and sonar or ultrasonic imaging of a biological body.

In JP-A-52-20857 (1977) and U.S. Pat. No. 4,140,022, there have been described such apparatuses that the reception signals are frequency-shifted into the low frequency signals by mixing the respective reception signals with the reference signals, the phases of which have been controlled, and thereafter the delays are applied to the low frequency signals so as to be summed with each other. In these apparatuses, it may be understood that the frequency-shift phasing methods are performed.

SUMMARY OF THE INVENTION

Even in such apparatuses for employing any of the above-described phasing methods, the delay amounts for the respective signals need to be changed in accordance with variations in the azimuth or distance in order to coincide the phases with each other. In general, to realize such delay amount changes under the limited cost of the apparatus, the delay unit for applying the delays is so constructed that selections are made of delay times analogous to the theoretical values of the delay times as to the reception signals from a limited number of plural delay times. In other words, the delay times are selected from values obtained or defined by multiplying a certain quantizing unit by an integer.

In accordance with the above-described frequency-shift phasing methods, even if the quantizing unit of the delay time of the delay unit is greater than the simple phasing method, sufficient azimuth resolution can be obtained. For instance, in one example as described in the above-described JP-A-52-20857 (1977), although the respective reception signals which have been frequency-shifted by way of the mixing process are sampled at a predetermined period, and the delay time amounts which are equal to a value obtained by multiplying this sampling period by an integer are realized, the sampling period can be set to a relatively large period. However, the highly precise phase control for the reference signals to be mixed with the respective reception signals must be performed in accordance with the wave fronts to be phased, and thus it is so difficult to arrange such a frequency shifting unit.

An object of the present invention is to provide a phase adjustment apparatus of an ultrasonic measuring device, capable of simplifying a phase control of a reference signal which is used in the frequency shift method, of lowering cost of a frequency shifting unit, and also of performing a correct phasing operation upon use of a short pulse.

Another object of the present invention is to provide such a phase adjustment apparatus of an ultrasonic measuring device, capable of adopting a large delay time unit for setting delay times at a main delay circuit after being frequency-shifted, whereby cost of the overall delay circuit can be reduced.

A basic construction of the phase adjustment apparatus according to the present invention resides in that small delay circuits are provided in front of the respective frequency shifting units for the reception signals of plural signal channels, and a main delay unit is provided after the frequency shifting-unit. The main delay circuit is a quantized delay circuit capable of selecting delay times for the respective reception signals from a plurality of delay times obtained by multiplying the unit delay time by an integer. The phasing operations of the respective reception signals are executed based on a total amount of the selected delay time and the delay times of the above-described small delay circuits, and then the resultant signals are added with each other, so that azimuth resolution is formed. Here, if the phases of the reference signals employed in the frequency shifting unit are common for all of the reception signal channels, namely the phase controls for the reference signals in accordance with the front waves to be phased are omitted, signal appearing times of the respective signal channels can be coincident with each other at the output of the main delay circuit. However, the phases of these signals do not generally coincide with each other. As a result, a signal for selectively indicating only reflection sound waves from a desirable azimuth or a desirable position cannot be obtained by the addition. Therefore, according to the present invention, the ratio of the delay time unit of the main delay circuit to one-cycle period of the reference signal used in the frequency shifting unit is selected to be an integer ratio.

First, if the delay time unit of the main delay circuit is equal to one-cycle period of the reference signal, or to a time unit obtained by multiplying this period by an integer, even when the phase of the reference signal is commonly used for all of the reception signal channels, since the phases of the outputs from the main delay circuit are coincident with each other, the signal for selectively indicating only the reflection sound waves from a desirable azimuth or a desirable position can be obtained with maintaining the above-described basic arrangement.

Next, when the ratio of the unit delay time of the main delay circuit to one-cycle period of the reference signal employed in the frequency shifting unit is selected to be an integer ratio of l to L ("L" being greater than or equal to 2), the outputs from the main delay circuit for the respective signal channels become L-sorts of phases as $2\pi m/L$ (m=0 to L−1) in accordance with the delay times selected in the main delay circuit. Accordingly, it is so arranged that the phase shifters capable of selecting the phase shift amount from $2\pi m/L$ (m=0 to L−1) are connected at the output sides or the input sides of the mixers for performing the frequency shift, and a selection for the amount of the phase shift at the phase shifters is made based upon a remainder when the delay time selected in the main delay circuit is divided by one-cycle period of the reference signal, whereby phase differences occurring in the outputs from the main delay circuit is removed. More specifically, when L=2, in other words, the unit delay time of the main delay circuit is equal to a half-cycle period of the reference signal employed in the frequency shifting unit, or to a value obtained by multiplying this half-cycle period by an odd number, inverters for inverting the signals in response to the delay times selected in the main delay circuit are employed instead of the phase shifters. Alternatively, instead of these circuit arrangements, a reference phase controller may be employed which selects the phases of the reference signals given to the respective mixers of the signal channels from $2\pi m/L$ (m=0 to L−1). Even in this case, the frequency shifting unit can be made simple, since it is possible to employ such an arrangement for selecting the phases of the reference signals supplied to the respective mixers of these signal channels from L-sorts of phases which have been previously prepared, instead of the precise phase controls for the reference signals in response to the wave fronts to be phased, which is required in the conventional frequency shift phasing apparatuses.

Other features of the present invention may be apparent from a detailed description of the invention.

DETAILED DESCRIPTION

Figure 1:
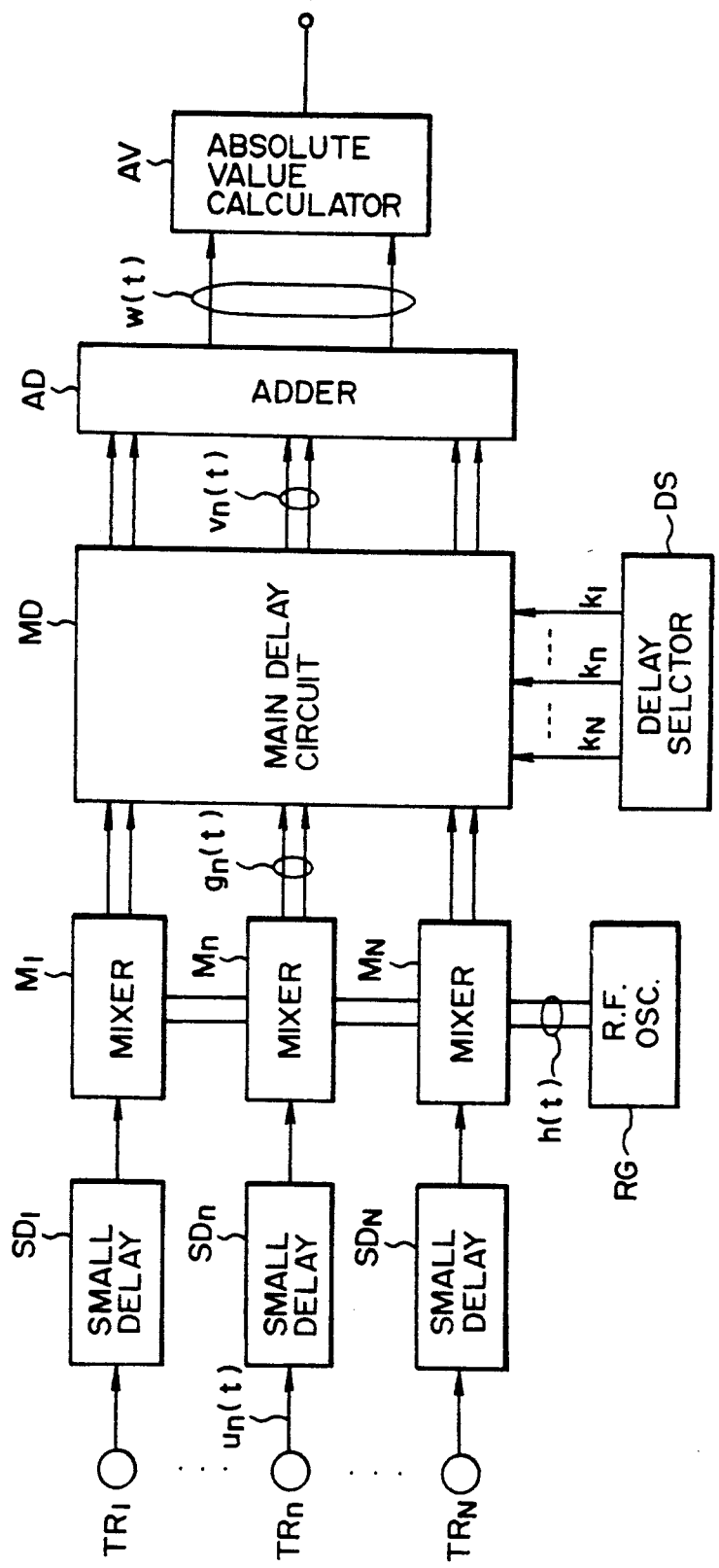
FIG. 1 is a schematic block diagram for explaining a basic arrangement of a phase adjustment apparatus according to the present invention.

FIG. 1 represents a circuit arrangement which will constitute a basic arrangement for various embodiments of the present invention. First of all, an operation of this circuit arrangement will now be considered. Reception signals from arrayed ultrasonic transducer elements $TR_1$ to $TR_N$ are delayed in small delay circuits $SD_1$ to $SD_N$, and these delayed signals are multiplied by a reference signal h(t) generated from a reference signal generator RG in mixers $M_1$ to $M_N$. The reference signals h(t) is a complex signal indicated by:

$$h(t) = \exp\{-j\omega_d t\}$$

That is to say, the reference signal corresponds to two sinusoidal signals each having a frequency of Wd and having different phases with each other at 90 degrees. The complex signals represented by low frequency components obtained from multiplication results are delayed respectively in a main delay circuit MD, the setting unit of delay time of which is "$\tau_Q$"; the delayed complex signals are added with each other in an adder AD so that one set of complex signals W(t) which have been phased with respect to either a desirable position, or a desirable azimuth; both a real part of the complex signal W(t) and an imaginary part thereof are squared respectively and then are added with each other; and a desirable reception signal is obtained from an absolute value calculator AV for calculating a square root of the added real and imaginary parts.

Assuming now that a transmission signal whose center frequency is $\omega_s$ is "s(t)", this signal s(t) is approximated to:

$$s(t) = A(t)\exp(j\omega_s t)$$

where symbol A(t) indicates an envelope form of the transmission signal. The reception signal Un(t) caused by this transmission signal at an n-th element of reflection sound wave from the above-described desirable position or desirable azimuth, is expressed as follows, assuming now that propagation time of the sound wave up to the n-th element is "$\tau_n$";

$$\begin{aligned} u_n(t) &= s(t - \tau_n) \\ &= A(t - \tau_n)\exp\{j\omega_s(t - \tau_n)\} \end{aligned}$$

In the main delay circuit MD, delay times of the respective signal channels are selected from a plurality of delay times that are equal to integer multiplication of a delay time unit "$\tau_Q$". The delay times $K_n\tau_Q$ of the respective signal channels are selected in a delay selector DS in such a manner that a total delay time with this delay time and a delay time "$\tau_{sn}$" caused by the small delay time $SD_n$ becomes:

$$k_n\tau_Q + \tau_{sn} = \tau_n$$

As a result, assuming now that a signal obtained by delaying the reception signal Un(t) in the small delay circuit is fn(t), this signal fn(t) is expressed by:

$$f_n(t) = A(t + k_n\tau_Q)\exp\{j\omega_s(t + k_n\tau_Q)\}$$

Furthermore, if the delays $K_n\tau_Q$ (Kn is an integer) which have been selected as described above, are given to this signal fn(t) in the main delay circuit MD, the reception signals of the respective element channels for the reflected sound waves from the above-explained desirable position or desirable azimuth, are generated at the same time instant of an output side of the main delay circuit MD. However, the reference signal h(t) applied to the mixers of the present circuit arrangement is commonly used for the element channels. As a consequence, a multiplication result "gn(t)" obtained from the mixer Mn is given by:

$$\begin{aligned} g_n(t) &= f_n(t)h(t) \\ &= A(t + k_n\tau_Q) \cdot \exp[j\{(\omega_s - \omega_d)t + k_n\omega_s\tau_Q\}] \\ &= A(t + k_n\tau_Q) \cdot \exp[j\{\omega't + k_n\omega_s\tau_Q\}] \\ &= A(t + k_n\tau_Q) \cdot \exp[j\{\omega't + k_n(\omega' + \omega_d)\tau_Q\}] \\ &= A(t + k_n\tau_Q) \cdot \exp[j\{\omega'(t + k_n\tau_Q) + k_n\omega_d\tau_Q\}] \end{aligned}$$

It should be noted that symbol $\omega'$ corresponds to a frequency which is obtained by frequency-shifting the frequency of the reference signal in the mixer, and is expressed by:

$$\omega_s - \omega' = \omega_d$$

A signal Vn(t) in which this waveform has been delay-processed by the main delay circuit MD with a delay time of "$K_n\tau_Q$", is given by:

$$V_n(t) = g_n(t - k_n \tau_Q)$$
$$= A(t)\exp[j\{\omega't + k_n\omega_d\tau_Q\}]$$
$$= A(t)\exp[j\{\omega't + 2\pi k_n\tau_Q/\tau_d\}]$$

It should also be noted that symbol "$\tau_d$" is period of the reference signal and is expressed by:

$$\omega_d = 2\pi/\tau_d$$

With respect to this signal, symbols "kn" are different from each other, depending on the channel number "n". As a consequence, generally speaking, phases of the respective channel outputs from the main delay circuit MD are not coincident with each other, and amplitude of a resultant output by adding these channel outputs with each other, namely, $$\omega(t) = \sum_{n=1}^{N} v_n(t)$$

In other words, generally speaking, a signal which is not increased selectively represents the reflection signals from the above-described position or desirable azimuth, cannot be obtained from the output of the adder circuit AD.

Accordingly, in accordance with the present invention, such an ultrasonic signal processing circuit is proposed even with the basic arrangement constructed of the small delays, mixing, and quantized delays as shown in FIG. 1 in that both timings of generation of output signals from the respective channels are coincident with each other, and also phases of these output signals therefrom are coincident with each other, and a signal for selectively indicating sound waves reflected from either a desirable position, or a desirable azimuth can be obtained by way of an adding method.

Figure 2:
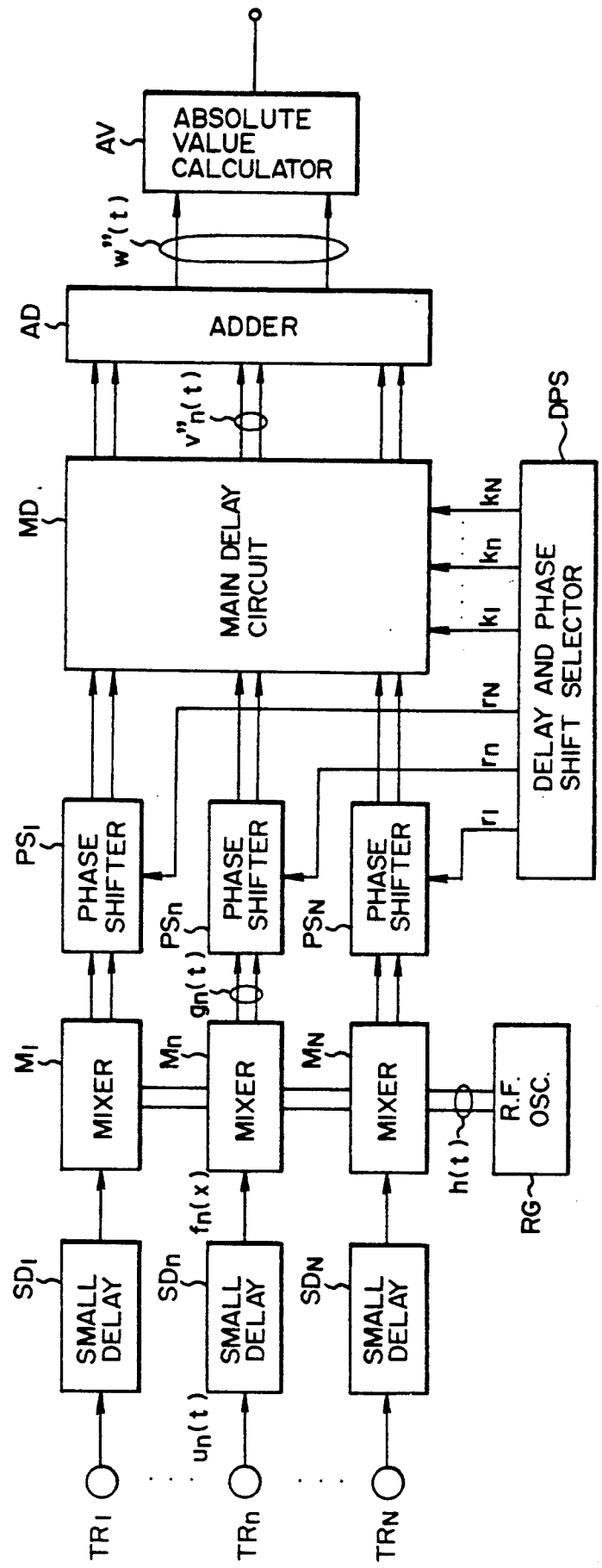
FIG. 2 is a schematic block diagram for showing an embodiment of the present invention.

FIG. 2 represents one embodiment of the present invention. The reception signals from the arranged ultrasonic transducer elements $TR_1$ to $TR_N$ are delayed in the respective small delay circuits $SD_1$ to $SD_N$, and then these delayed signals are multiplied by the reference signal h(t) generated from the reference signal generator RG in the mixers $M_1$ to $M_N$. After the low frequency signal components produced in the respective mixers $M_1$ to $M_N$ have been shifted by phase shifters $PS_1$ to $PS_N$, the phase-shifted low frequency signals are delayed respectively in the main delay circuit MD. The delayed low frequency components are added with each other in the adder AD and then the added complex signal is converted into an absolute value signal in the absolute value calculator AV. It should be noted that the signals to be inputted into the small delay circuits $SD_1$ to $SD_N$ may not be the reception signals directly from the arrayed ultrasonic transducer elements $TR_1$ to $TR_N$. For instance, reception signals which have been amplified by preamplifiers, or reception signals from each of plural element groups which constitute the arrayed ultrasonic transducer elements may be used.

Also in the embodiment shown in FIG. 2, the main delay circuit MD is a quantized delay circuit capable of selecting the delay times of the respective signal channels from a plurality of delay times that are obtained by multiplying the delay time unit "$\tau_Q$" by an integer. In response to a selection control signal derived from a delay and phase shift selector DPS, the delay time of the respective signal channels of the main delay circuit MD is selected in order satisfy the following relationship:

$$K_n\tau_Q + \tau_{Sn} = \tau_n$$

Furthermore, in this embodiment, it is so set such a relationship between the delay time unit "$\tau_Q$" of this main delay circuit and the period "$\tau_d$" of the reference signal h(t) when "L" and "I" being integers;

$$\tau_Q = (I/L)\tau_d$$

That is to say, a ratio of "$\tau_d$" to "$\tau_Q$" is equal to an integer ratio. As to the frequency "$\omega_d$" of the reference signal h(t), it is given:

$$\omega_d = 2\pi \frac{I}{L} \cdot \frac{1}{\tau_Q} = \frac{2\pi}{\tau_d}$$

At this time, if the phase shifters $PS_1$ to $PS_N$ were not inserted in the circuit arrangement of this embodiment, the outputs Vn(t) of the respective channels of the main delay circuit MD are given as follows:

$$V_n(t) = A(t)\exp[j\{\omega't + 2\pi k_n\tau_Q/\tau_d\}]$$
$$= A(t)\exp[j\{\omega't + 2\pi k_n(I/L)\}]$$
$$= A(t)\exp[j\{\omega't + (2\pi/L)k_nI\}]$$

That is to say, the phases of the respective channel signals are rotated in a unit of $2\pi/L$ corresponding to the value of Kn. Therefore, phase shifters, phase shift amounts of which can be selected to be any of $2m\pi/L$ (m=0 to L−1), are employed as the phase shifters $PS_1$ to $PS_N$, and thus the phase shift amounts of the respective phase shifters $PS_1$ to $PS_N$ are selected in accordance with the delay amounts $Kn\tau_Q$ (n=1 to N) of the respective channels of the main delay circuit MD. More concretely speaking, the delay/phase shift selector DPS employs the coefficient Kn of the delay amount $Kn\tau_Q$ for each of the channels of the main delay circuit MD, and calculates a remainder "$r_n$" when KnI is divided by L. Then, the selection control signals are produced in such a manner that the respective phase shift amounts of the phase shifters $PS_1$ to $PS_N$ become $2r_n\pi/L$ (n=1 to N) and are supplied to the respective phase shifter. As a consequence, with respect to the reflection signals from the desirable position or the desirable azimuth, output signals Vn"(t) from all channels of the main delay circuit MD may be equal to;

$$V_n''(t) = A(t)\exp[j\omega't]$$

As previously described, when both the envelope shapes and phases of the signals in all of the channels are coincident with each other, and the resultant signals are added with each other in the adder AD, a result of this addition W'''(t) is expressed by:

$$W'''(t) = \sum_{n=1}^{N} V_n''(t) = NA(t)\exp[j\omega't],$$

whereby amplitudes thereof are grown. In other words, the signal selectively indicative of the reflection signals from either the above-described position, or the desirable azimuth can be obtained.

Now, an operation of a specific example of the arrangement shown in FIG. 2 will be described in which L=1, namely the setting unit $\tau_Q$ of the delay time of the main delay circuit MD is equal to either the period "$\tau_d$" of the reference signal h(t), or a method obtained by multiplying this period "$\tau_d$" by an integer. A channel output Vn(t) in this case is given by:

$$V_n(t) = A(t)\exp[j\{\omega't + 2\pi k_n(I/L)\}]$$
$$= A(t)\exp[j\{\omega't + 2\pi k_n I\}]$$
$$= A(t)\exp[j\omega't]$$

In this case, all of the signals have the completely same waveforms without employment of the phase shifters $PS_1$ to $PS_N$. As a result, W(t) obtained by adding these signals with each other is expressed by:

$$W(t) = \sum_{n=1}^{N} v_n(t) = NA(t)\exp[j\omega't]$$

and the amplitude thereof is greatly grown by the adding operation without receiving variations in the envelope shapes. Consequently, phasing operation can be achieved in the arrangement shown in FIG. 1 from which the phase shifters have been omitted. In the concrete example of the apparatus arrangement under such a condition of L=1, $\tau_Q = \tau_d = 100$ n sec., the setting unit $\tau_Q$ of the delay time of the main delay circuit MD is equal to 100 n sec., and the reference signal's frequency is 10 MHz in accordance with, for instance, I=L=1.

Subsequently, a description will now be made of such a case that L=2. In this case, $\tau_Q/\tau_d = I/L = \frac{1}{2}$, 3/2, 5/2, ···, and I must be an odd number. In other words, the unit delay time "$\tau_Q$" of the main delay circuit MD is equal to a half-cycle period of the reference signal, or a period obtained by multiplying the half-cycle period by an odd number. Outputs Vn(t) of the respective channels of the main delay circuit MD are given by:

$$v_n(t) = A(t)\exp[j\{\omega't + 2\pi k_n(I/L)\}]$$
$$= A(t)\exp[j\{\omega't + \pi k_n I\}]$$
$$= \begin{cases} A(t)\exp[j\omega't] & (k_n: \text{even number}) \\ A(t)\exp[j\{\omega't + \pi\}] & (k_n: \text{odd number}) \end{cases}$$

Figure 3:
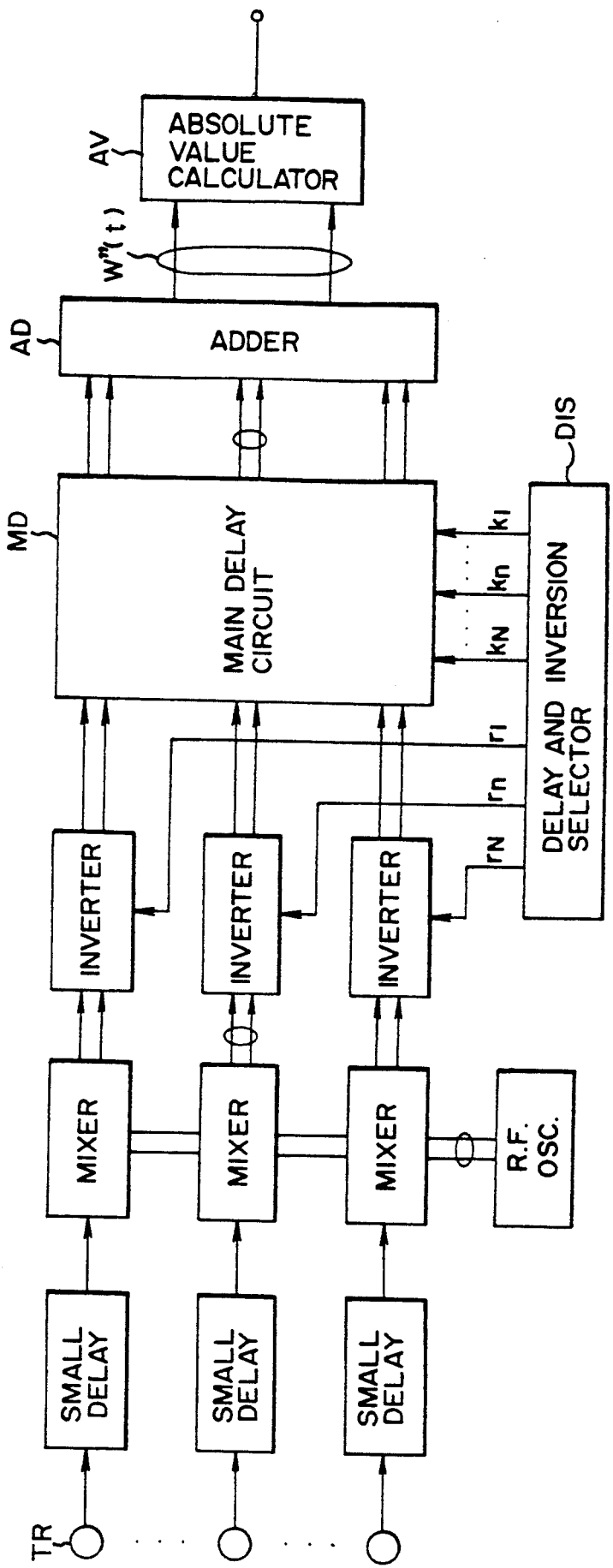
FIG. 3 is a schematic block diagram for representing another embodiment.

As described above, the phases of the respective signals are inverted in case of either an odd number, or an even number, respectively. Accordingly, an arrangement shown in FIG. 3 in which inverters $IN_1$ to $IN_N$ are employed instead of the phase shifters $PS_1$ to $PS_N$ represented in FIG. 2, may be employed. When the coefficient Kn of the delay time $Kn\tau_Q$ of the signal channels of the main delay circuit MD is equal to an even number, a delay/inversion selector DIS causes the inverting operation of the inverter of this signal channel to be interrupted. When the coefficient "Kn" is equal to an odd number, the delay/inversion selector DIS causes the inverting operation of the inverter of this signal channel to be performed, due to such a selective phase inversion, all of the signals V'n(t) become:

$$V_n'(t) = A(t)\exp[j\omega't].$$

and then the waveforms of these signals are completely identical to each other. As a result, a summation result W'(t) of these signals is given by:

$$W(t) = \sum_{n=1}^{N} v_n'(t) = NA(t)\exp[j\omega't]$$

Accordingly, it is possible to obtain a signals for selectively indicating the reflection sound waves from the desirable position, or desirable azimuth. In the concrete example of the embodiment shown in FIG. 3, for instance, in accordance with L=2 and I=3, $\tau_Q = 120$ n sec., $\tau_d = 80$ n sec., the set unit of the delay time of the main delay circuit MD is 120 n sec., and the frequency of the reference signal is 12.5 MHz.

Figure 4:
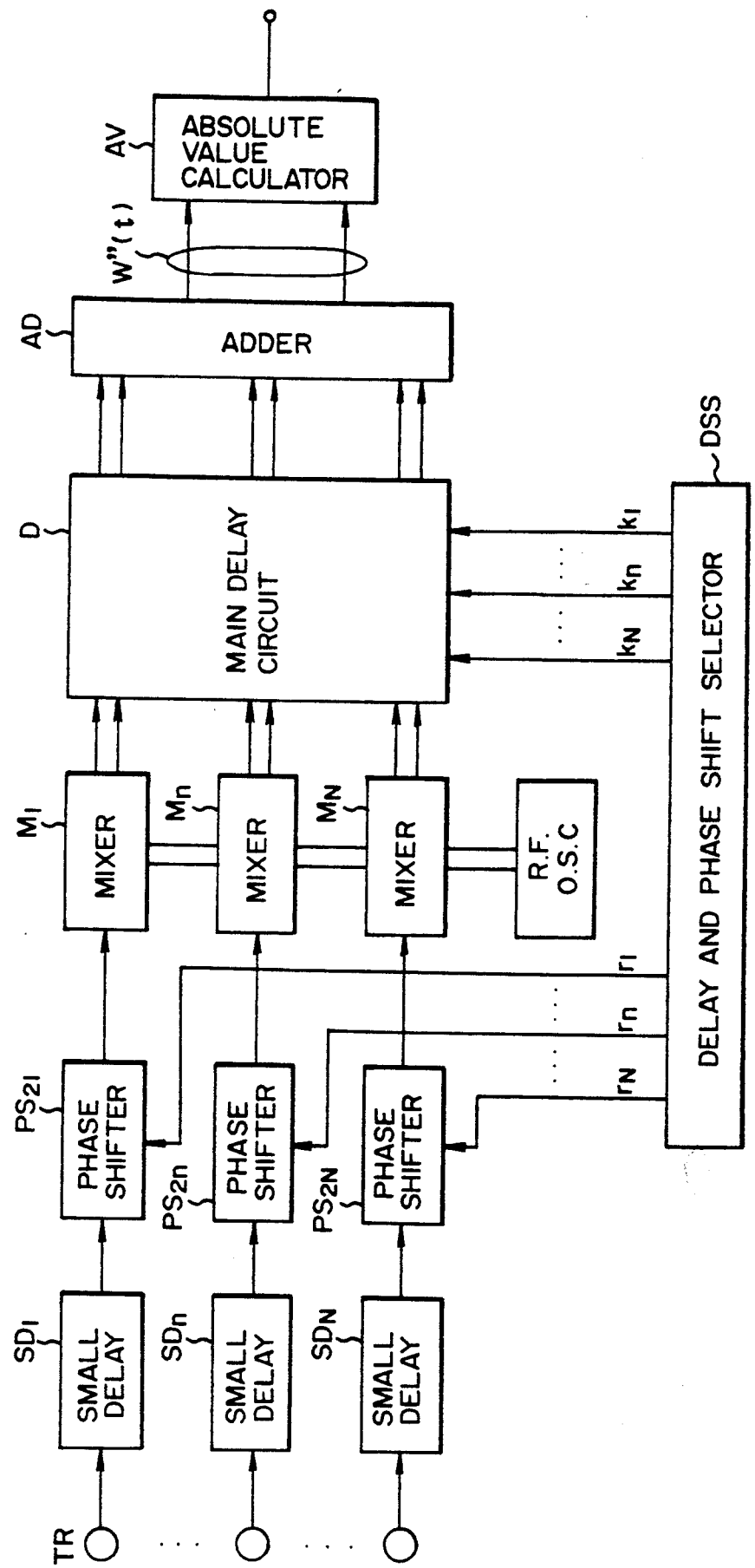
FIG. 4 is a schematic block diagram for showing a further embodiment.

FIG. 4 represents a further embodiment of the present invention. In this embodiment, instead of the phase shifters $PS_1$ to $PS_N$ employed in the embodiment shown in FIG. 2, phase shifters $PS_{21}$ to $PS_{2N}$ are connected to the outputs to $SD_N$. Since the operations of the mixers are linear with regard to the fixed phase angle, the same effects or results are obtained even when the phase shifters provided at the output sides of the mixers $M_1$ to $M_N$ are moved to the input sides thereof. As a consequence, the phase shifting amounts "$\phi n$" selected in the respective phase shifters $PS_{21}$ to $PS_{2N}$ are $2m\pi/L$ (m=0 to L−1). A delay and phase shift selector DPS selects delay times "$Kn\tau_Q$" of the respective channels of the main delay circuit MD, and also selects a value of $\phi n$ in accordance with a remainder "$r_n$" obtained when KnI is divided by L, which is similar to that of the embodiment shown in FIG. 2. It should be noted that a delay line may be employed other than the normal phase shifter as the phase shifters $PS_1$ to $PS_N$.

Figure 5:
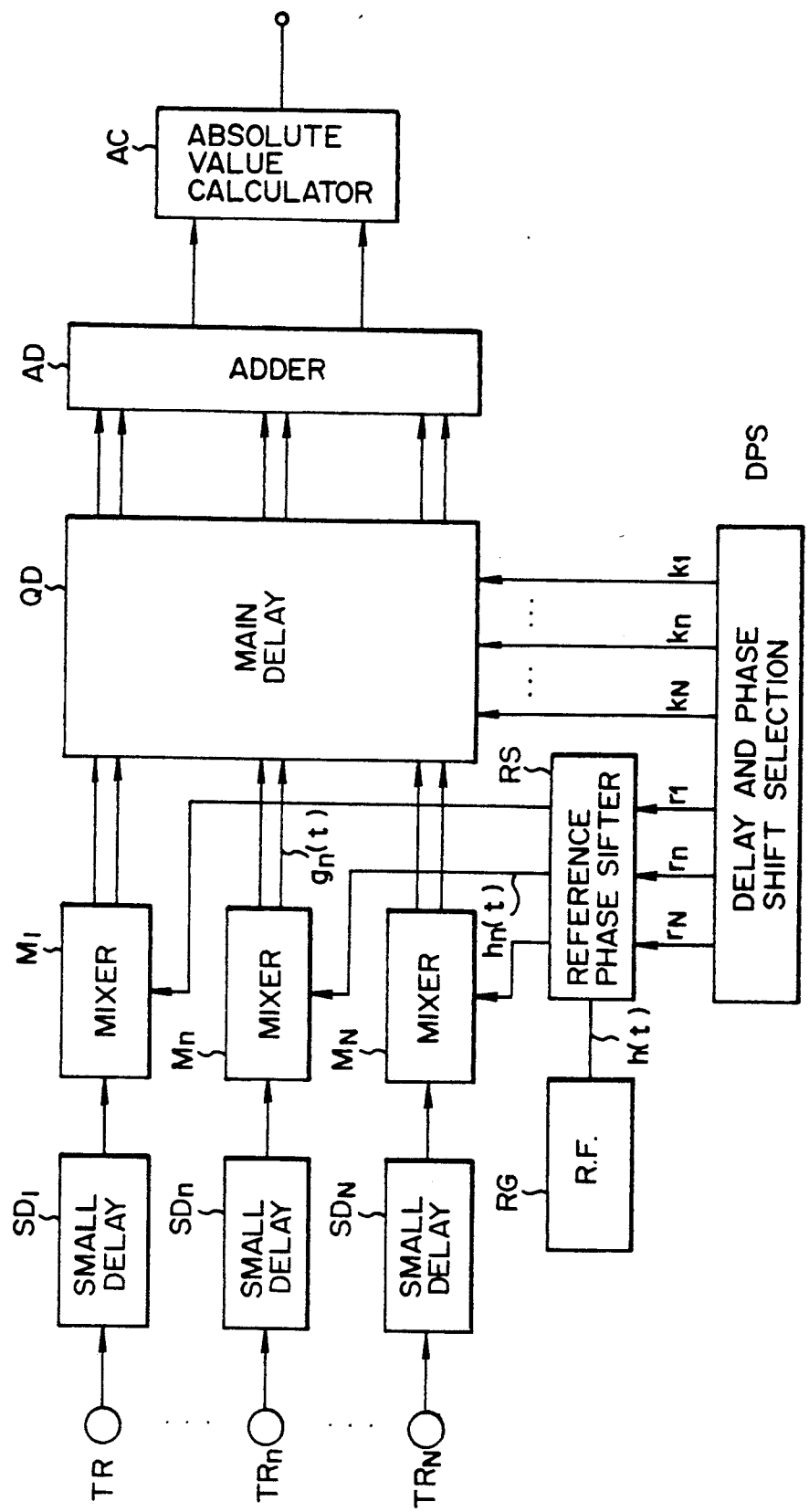
FIG. 5 is a schematic block diagram for showing a delay circuit of a still further embodiment; and, FIG. 6 is a schematic block diagram for showing a concrete embodiment of a main delay circuit employed in these embodiments.

FIG. 5 represents a still further embodiment of the present invention. In accordance with this embodiment, the phase shifters employed in the embodiment shown in either FIG. 2, or FIG. 4 are omitted, and a phase control of the reference signal hn(t) is performed by a reference signal phase shifter RC, instead of these phase shifters, which is supplied to mixers in the respective channels.

The reference signal h(t) produced from a high frequency oscillator RG is given as:

$$h(t) = \exp\{-j\omega_d t\}$$

Assuming now that a phase shift amount "$\phi n$" of the reference signal supplied to an n-th channel and shifted by the reference signal phase shifter RC is "$\phi n$", the output signal hn(t) of the reference signal phase shifter RC becomes:

$$h_n(t) = h(t)\exp\{-j\phi_n\}$$

As a consequence, assuming now that a multiplication result obtained from the mixer Mn is gn(t), it is given:

$$g_n(t) = f_n(t)h(t)\exp\{-j\phi_n\}$$
$$= A(t + k_n\tau_Q) \cdot$$
$$\exp[j\{\omega'(t + k_n\tau_Q) + k_n\omega_d\tau_Q - \phi_n\}]$$

A signal Vn(t) obtained by time-delaying this signal waveform by $Kn\tau_Q$ in a quantized delay circuit QD, is expressed by:

$$V_n(t) = g_n(t - k_n\tau_Q)$$
$$= A(t)\exp[j\{\omega't + k_n\omega_d\tau_Q - \phi_n\}]$$
$$= A(t)\exp[j\{\omega't + 2\pi k_n\tau_Q/\tau_d - \phi_n\}]$$

Thus, if the phase shift amount $\phi_n$ of the reference signal phase shifter RS is set as:

$$\phi_n = 2\pi k_n\tau_Q/\tau_d$$

outputs $V_n'''(t)$ of the mixers with respect to all of channels $n=1$ to N become:

$$V_n'''(t) = A(t)\exp[j\omega't]$$

All of these outputs have the completely same waveforms. As a result, an adding result $W'''(t)$ from the adder AD is expressed by:

$$w'''(t) = \sum_{n=1}^{N} v_n'''(t) = NA(t)\exp[j\omega't]$$

Then, a signal for selectively representing the reflection signals from the desirable position, or desirable azimuth can be obtained. Also in this embodiment, if a ratio of the setting unit $\tau_Q$ of the delay time for the quantized delay circuit QD, to the period $\tau_d$ of the reference signal h(t) is selected to be an integer ratio of I to L, a phase shift amount $\phi_n$ of the reference signal caused by the reference signal control unit RC is given as follows:

$$\phi_n = 2k_n I\pi/L$$

Therefore, in this case, the delay and phase shift selector DPS selects the delay times of the respective signal channels for the main delay circuit to be $Kn\tau_Q$, and also selects the phase shift amount $\phi_n$ of the reference signals of the respective signal channels in the reference signal phase shifter RS in such a manner that the phase shift amount $\phi_n$ is selected to be as follows, in accordance with the remainder "$r_n$" when knI is divided by L:

$$\phi_n = 2\pi r_n/L$$

As described above, since the phase shift amounts of the reference signal caused by the reference signal phase shifter RS can be selected from L sorts of phase shift amounts, the arrangement of the apparatus can be made simple.

In the above-explained various embodiments, the reference signal was the complex signal and all of the respective blocks provided after the mixers handled the complex signals. However, the present invention is not limited such arrangements, but a simple arrangement capable of handling only the real part or the imaginary part of the complex signal may be employed. As previously explained, in such a simple arrangement capable of signal-processing only the real part or imaginary part, the absolute value calculator AC is no longer required.

Figure 6:
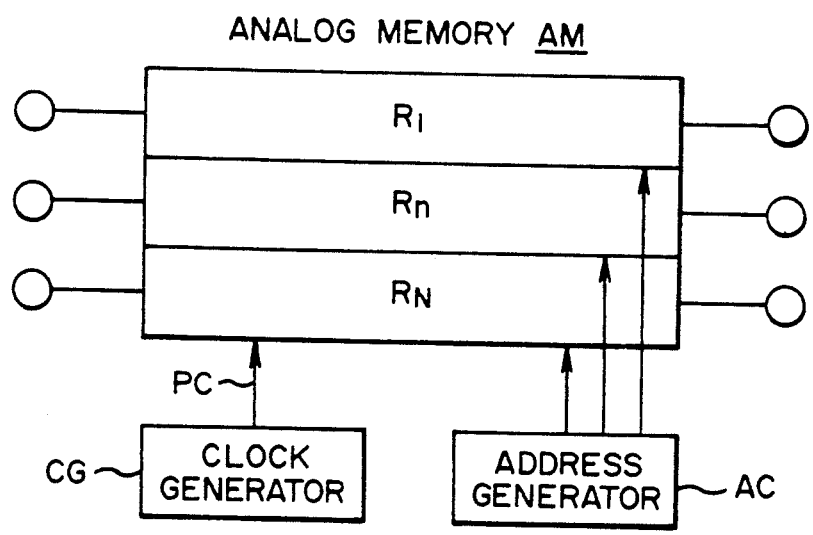

In FIG. 6, it is possible to employ a circuit for realizing a delay in a storage circuit of a sampled signal, since the setting unit of the delay time is quantized in the quantized delay circuits QD in the above various embodiments. FIG. 6 is a concrete circuit example of such a delay circuit. Symbols $R_1$, $R_n$, $R_N$ indicate an analog memory having a plurality of storage addresses, and the reception signals of the respective channels (the reception signals which have been processed by the mixers to produce low-frequency components) are sampled respectively and then stored into the respective memories. The storage, namely the sampling timing is performed in synchronization with a clock signal CP having a period "$\tau_c$" which are generated from a clock oscillator CG. Also, the stored signals are read out in synchronization with the clock signal CP. It should be noted that both the storage addresses and the read addresses are sequentially controlled by an address controller AC, and then the delay time is determined, depending upon when the stored information is read out, starting from the first clock. Basically, although it is set to $\tau_c = \tau_Q$, it may be set to $2\tau_c = \tau_Q$ since $\tau_c$ must selected to be small, depending upon the signal frequency.

As apparent from the foregoing descriptions, the cost of the apparatus can be lowered with correct phasing effects by combining the small delay circuits with the down-frequency mixing and quantizing delay circuits in any of these embodiments. More specifically, a specific attention should be paid to such a fact that assuming now that the ratio of the set unit $\tau_Q$ of the delay time in the quantized delay circuit QD, to the period $\tau_d$ of the reference signal h(t) is selected to be an integer ratio of I to L, the phase shift amounts which should be prepared in the phase shifters or the reference signal phase shifter employed in the respective channels, become L sorts of delay times. To avoid such a problem that either the phase shifters or the reference signal phase shifter becomes complex, it is preferable to select the values of $\tau_Q$ and $\tau_d$ in such a manner that "L" does not exceed 16.

What is claimed is:

1. A phase adjustment apparatus of an ultrasonic measuring device for producing a signal for selectively indicating reflection signals from a desirable position of a desirable azimuth by signal-processing a plurality of reception signals obtained from an array of ultrasonic converting devices which receive ultrasonic waves at a plurality of receiving positions, said phasing apparatus comprising:

a plurality of small delay circuits for applying compensation delay for a remainder of a main delay to each of said plural reception signals;

a plurality of mixers for mixing a plurality of signals derived from said small delay circuits with reference signals each having a same frequency to acquire different frequency components; and a main delay circuit for applying delays to respective outputs of said mixers and for compensating differences in propagation times of the ultrasonic waves propagated from said desirable position or desirable azimuth to said plural receiving positions based upon a total delay amount of acoustic propagation delays and also the compensation time delay of the small delay circuits.

2. A phase adjustment apparatus of an ultrasonic measuring device for producing a signal for selectively indicating reflection signals from a desirable position or a desirable azimuth by signal-processing a plurality of reception signals obtained from an array of ultrasonic converting devices which receive ultrasonic waves at a plurality of receiving positions, said phasing apparatus comprising:

a plurality of small delay circuits for applying compensation delay for a remainder of a main delay to each of said plural reception signals;

a plurality of mixers for mixing a plurality of signals derived from said small delay circuits with reference signals each having a same frequency to acquire different frequency components;

a plurality of phase shifters for shifting respective outputs from said mixers; and, a main delay circuit for applying delays to respective outputs of said phase shifters and for compensating differences in propagation times of the ultrasonic waves propagated from said desirable position or desirable azimuth to said plural receiving positions based upon a total delay amount of acoustic propagation delays and also the compensation time delay of the small delay circuits, phase shift amounts of said plurality of phase shifters corresponding to phase shift amounts for compensating differences in phases of outputs from respective signal channels of said main delay circuit, which are determined by a ratio of the delays of said main delay circuit in the respective signal channels to one-cycle period of said reference signal.

3. A phase adjustment apparatus of an ultrasonic measuring device as claimed in claim 2, wherein said main delay circuit corresponds to a quantized delay circuit for applying a delay time which has been selected from a plurality of delay times obtained by multiplying a predetermined delay time unit by an integer, and a ratio of said unit delay time to said period of the reference signal is an integer ratio.

4. A phase adjustment apparatus of an ultrasonic measuring device for producing a signal for selectively indicating reflection signals from a desirable position or a desirable azimuth by signal-processing a plurality of reception signals obtained from an array of ultrasonic converting devices which receive ultrasonic waves at a plurality of receiving positions, said adjustment apparatus comprising:

a plurality of small delay circuit for applying compensation delay for a remainder of a main delay to each of said plural reception signals;

a plurality of mixers for mixing a plurality of signals derived from said small delay circuits with reference signals each having a same frequency to acquire different frequency components;

a plurality of phase shifters capable of selecting plural phase shift amounts, and for phase-shifting respective outputs from said mixers;

a main delay circuit for applying to outputs from said plurality of phase shifters, delays selected from a plurality of delay times which are obtained by multiplying a predetermined delay time unit by an integer, and for compensating differences in propagation times of the ultrasonic waves propagated from said desirable position or desirable azimuth to said plural receiving positions based upon a total delay amount of acoustic propagation delays and also the compensation time delay of the small delay circuits, a ratio of said unit delay time to said one-cycle period of the reference signals being equal to an integer ratio of I to L; and phase shift amount selecting means for selecting respective phase shift amounts of said plural phase shifters corresponding to delays in respective signal channels of said main delay circuit.

5. A phase adjustment apparatus of an ultrasonic measuring device for producing a signal for selectively indicating reflection signals from a desirable position or a desirable azimuth by signal-processing a plurality of reception signals obtained from an array of ultrasonic converting devices which receive ultrasonic waves at a plurality of receiving positions, said phase adjustment apparatus comprising:

a plurality of small delay circuits for applying compensation delay for a remainder of a main delay to each of said plural reception signals;

a plurality of mixers for mixing a plurality of signals derived from said small delay circuits with reference signals each having a same frequency to acquire different frequency components;

a plurality of phase shifters capable of selecting plural phase shift amounts, and for phase-shifting respective outputs from said mixers;

a main delay circuit delaying respective outputs from said plurality of phase shifters, delay times being selectable from a plurality of delay times obtained by multiplying a predetermined delay time unit by an integral, and a ratio of said unit delay time to one-cycle period of said reference signal being an integer ratio of I to L; and delay time/phase shift amount selecting means for selecting the respective delay times of said main delay circuit to be a value obtained by multiplying said unit delay time by Kn ("n" being the number of signal channel), and also for selecting the respective phase shift amounts of said plural phase shifters based upon a remainder "$r_n$" of KnI divided by L in order to compensate differences in propagation times of the ultrasonic waves propagated from said desirable position or desirable azimuth to said plural receiving positions based upon a total delay amount of acoustic propagation delays and also the compensation time delay of the small delay circuits.

6. A phase adjustment apparatus of an ultrasonic measuring device as claimed in claim 5, wherein the value of L does not exceed 16.

7. A phase adjustment apparatus of an ultrasonic measuring device for producing a signal for selectively indicating reflection signals from a desirable position or a desirable azimuth by signal-processing a plurality of reception signals obtained from an array of ultrasonic converting devices which receive ultrasonic waves at a plurality of receiving positions, said adjustment apparatus comprising:

a plurality of small delay circuits for applying compensation delay for a remainder of a main delay to each of said plural reception signals;

a plurality of phase shifters capable of selecting plural phase shift amounts and for phase shifting respective outputs from said small delay circuits;

a plurality of mixers for mixing a plurality of signals derived from said phase shifters with reference signals each having a same frequency to acquire different frequency components;

a main delay circuit for applying delays to the outputs from said plurality of mixers, said delays being selected from a plurality of delay times obtained by multiplying a predetermined delay time unit by an integer, and for compensating differences in propagation times of the ultrasonic waves propagated from said desirable position or desirable azimuth to said plural receiving positions based upon a total delay amount of acoustic propagation delays and also the compensation time delay of the small delay circuits, a ratio of said delay time unit to one-cycle period of said reference signals being an integer ratio of I to L; and phase-shift-amount selecting means for selecting respective phase shift amounts of said plural phase shifters based upon the delays in respective signal channels of said main delay circuit.

8. A phase adjusting apparatus of an ultrasonic measuring device for producing a signal for selectively indicating reflection signals form a desirable position or a desirable azimuth by signal-processing a plurality of reception signals obtained from an array of ultrasonic converting devices which receive ultrasonic waves at a plurality of receiving positions, said adjustment apparatus comprising:

- a plurality of small delay circuits for applying compensation delay for a remainder of a main delay to each of said plural reception signals;
- a plurality of phase shifters capable of selecting plural phase shift amounts and for phase-shifting, respective outputs from said small delay circuits;
- a plurality of mixers for mixing a plurality of signals derived from said phase shifters with reference signals each having a same frequency to acquire different frequency components;
- a main delay circuit for delaying respective outputs from said plurality of phase shifters, respective delay times being selectable from a plurality of delay times obtained by multiplying a predetermined delay time unit by an integral, and a ratio of said unit delay time to one period of said reference signal being an integer ratio of I to L; and,
- delay time/phase shift amount selecting means for selecting respective delay times of said main delay circuit to be a value obtained by multiplying said unit delay time by kn ("n" being the number of signal channel), and also for selecting respective phase shift amounts of said plural phase shifters based upon a remainder "$r_n$" of KnI divided by L in order to compensate differences in propagation times of the ultrasonic waves propagated from said desirable position or desirable azimuth to said plural receiving positions based upon a total delay amount of acoustic propagation delays and the compensation time delay of the small delay circuits.

9. A phase adjustment apparatus of an ultrasonic measuring device as claimed in claim 8, wherein the value of L does not exceed 16.

10. A phase adjustment apparatus of an ultrasonic measuring device for producing a signal for selectively indicating reflection signals from a desirable position or a desirable azimuth by signal-processing a plurality of reception signals obtained from an array of ultrasonic converting devices which receive ultrasonic waves at a plurality of receiving positions, said adjustment apparatus comprising:

- a plurality of small delay circuits for applying compensation delay for a remainder of a main delay to each of said plural reception signals;
- a plurality of mixers for mixing a plurality of signals from said small delay circuits with reference signals each having a same frequency and phases selected from plural phases so as to obtain different frequency components;
- a main delay circuit for applying to the outputs from said plurality of phase shifters, delays selected from a plurality of delay times which are obtained by multiplying a predetermined delay time unit by an integer, and for compensating differences in propagation times of the ultrasonic waves propagated from said desirable position or desirable azimuth to said plural receiving positions based upon a total delay amount of acoustic propagation delays and the compensation time delay of the small delay circuits, a ratio of said delay time unit to said one-cycle period of the reference signal being equal to an integer ratio of I to L; and
- reference phase selecting means for selecting the phases of the respective reference signals to said plurality of mixers in accordance with the delays of the main delay circuit in respective signal channels.

11. A phase adjustment apparatus of an ultrasonic measuring device for producing a signal for selectively indicating reflection signals from a desirable position or a desirable azimuth by signal-processing a plurality of reception signals obtained form an array of ultrasonic converting devices which receive ultrasonic waves at a plurality of receiving positions, said adjustment apparatus comprising:

- a plurality of small delay circuits for applying compensation delay for a remainder of a main delay to each of said plural reception signals;
- a plurality of mixers for mixing a plurality of signals from said small delay circuits with reference signals each having a same frequency and phases selected from plural phases so as to obtain different frequency components;
- a plurality of phase shifters capable of selecting plural phase shift amounts and for phase-shifting the respective outputs from said small delay circuits;
- a main delay circuit for delaying respective outputs from said plurality of phase shifters, respective delay times being selectable from a plurality of delay times obtained by multiplying a predetermined delay time unit by an integer, and a ratio of said delay time unit to one period of said reference signals being an integer ratio of I to L; and,
- delay time/phase shift amount selecting means for selecting respective delay times of said main delay circuit to be a value obtained by multiplying said unit delay time by Kn ("n" being the number of signal channel), and also for selecting respective phase shift amounts of said plural phase shifters based upon a remainder "$r_n$" of KnI is divided by L in order to compensate differences in propagation times of the ultrasonic waves propagated from said desirable position or desirable azimuth to said plural receiving positions based upon a total delay amount of acoustic propagation delays and the compensation time delay of the small delay circuits.

12. A phase adjustment apparatus of an ultrasonic measuring device as claimed in claim 11, wherein the value of L does not exceed 16.

13. A phase adjustment apparatus of an ultrasonic measuring device for producing a signal for selectively indicating reflection signals from a desirable position or a desirable azimuth by signal-processing a plurality of reception signals obtained form an array of ultrasonic converting devices which receive ultrasonic waves at a plurality of receiving positions, said adjustment apparatus comprising:

- a plurality of small delay circuits for applying compensation delay for a remainder of a main delay to each of said plural reception signals;

a plurality of mixers for mixing a plurality of signals from said small delay circuits with reference signals each having a same frequency to acquire different frequency components;

a plurality of inverters connected to each output of said mixers, for selectively inverting respective mixer outputs;

a main delay circuit for delaying outputs from said plurality of inverters, and capable of selecting delay times from a plurality of delay times which are obtained by multiplying a predetermined delay time unit by an integer, said delay time unit being equal to a half-cycle period of said reference signal, or a time obtained by multiplying said half-cycle period by an odd number; and, delay time/signal inversion selecting means for selecting respective delay times of said main delay circuit to be a value obtained by multiplying said unit delay time by Kn ("n" being the number of signal channel), and also for causing the corresponding inverter of the signal channel only when kn is an odd number to perform a signal inverting operation in order to compensate differences in propagation times of the ultrasonic waves propagated from said desirable position or desirable azimuth to said plural receiving positions based upon a total delay amount of acoustic propagation delays and the compensation time delay of the small delay circuits.

14. A phase adjustment apparatus of an ultrasonic measuring device for producing a signal for selectively indicating reflection signals form a desirable position or a desirable azimuth by signal-processing a plurality of reception signals obtained form an array of ultrasonic converting devices which receive ultrasonic waves at a plurality of receiving positions, said adjustment apparatus comprising:

a plurality of small delay circuits for applying compensation delays for a remainder of a main delay to each of said plural reception signals;

a plurality of mixers for mixing a plurality of signals derived from said small delay circuits with reference signals each having a same frequency to acquire different frequency components; and a main delay circuit for applying delays selected from a plurality of delay times which are obtained by multiplying a predetermined delay time unit to respective outputs of said mixers and for compensating differences in propagation times of the ultrasonic waves propagated from said desirable position or desirable azimuth to said plural receiving positions based upon a total delay amount of acoustic propagation delays and also the compensation time delay of the small delay circuit, said delay time unit being equal to either one-cycle period of said reference signals, or an integer multiplication thereof.

* * * * *